(12) United States Patent
Hennig (10) Patent No.: US 10,955,418 B2
(45) Date of Patent: Mar. 23, 2021

(54) METHOD OF DETERMINING THE PRESENCE AND/OR AMOUNT OF TARGET MOLECULES

(71) Applicant: Zellkraftwerk GmbH, Leipzig (DE)

(72) Inventor: Christian Hennig, Hannover (DE)

(73) Assignee: Zellkraftwerk GmbH, Leipzig (DE)

( * ) Notice: Subject to any disclaimer, the term of this patent is extended or adjusted under 35 U.S.C. 154(b) by 190 days.

(21) Appl. No.: 15/708,221

(22) Filed: Sep. 19, 2017

(65) Prior Publication Data

US 2018/0100860 A1    Apr. 12, 2018

(30) Foreign Application Priority Data

Sep. 19, 2016    (EP) .................................... 16189483

(51) Int. Cl.

| | |
|---|---|
| G01N 33/543 | (2006.01) |
| G01N 33/537 | (2006.01) |
| G01N 33/542 | (2006.01) |
| G01N 33/58 | (2006.01) |
| G01N 33/569 | (2006.01) |
| G01N 15/14 | (2006.01) |
| C12Q 1/6804 | (2018.01) |
| G01N 33/53 | (2006.01) |
| G01N 33/566 | (2006.01) |
| G01N 15/10 | (2006.01) |

(52) U.S. Cl.
CPC ......... *G01N 33/582* (2013.01); *C12Q 1/6804* (2013.01); *G01N 15/1463* (2013.01); *G01N 33/537* (2013.01); *G01N 33/5308* (2013.01); *G01N 33/542* (2013.01); *G01N 33/543* (2013.01); *G01N 33/5436* (2013.01); *G01N 33/54353* (2013.01); *G01N 33/54366* (2013.01); *G01N 33/566* (2013.01); *G01N 33/56966* (2013.01); *G01N 33/56972* (2013.01); *C07K 2317/92* (2013.01); *C07K 2317/94* (2013.01); *C07K 2319/035* (2013.01); *G01N 2015/1006* (2013.01); *G01N 2015/1486* (2013.01); *G01N 2015/1488* (2013.01)

(58) Field of Classification Search
CPC ............. G01N 33/582; G01N 33/5308; G01N 33/537; G01N 33/542; G01N 33/543; G01N 33/54353; G01N 33/5436; G01N 33/33; G01N 33/54366; G01N 33/533; G01N 33/56966; G01N 33/56972; G01N 15/1463
See application file for complete search history.

(56) References Cited

U.S. PATENT DOCUMENTS

| | | |
|---|---|---|
| 2011/0311966 A1 | 12/2011 | Hennig et al. |
| 2012/0129193 A1 | 5/2012 | Hennig et al. |
| 2016/0178490 A1* | 6/2016 | Civel .................. C12M 47/04 |

FOREIGN PATENT DOCUMENTS

| | | |
|---|---|---|
| WO | 2010049430 A1 | 5/2010 |
| WO | 2010070037 A1 | 6/2010 |

OTHER PUBLICATIONS

Hennig et al. A Versatile Platform for Comprehensive Chip-Based Explorative Cytometry. Cytometry Part A. 75A: 362-370 (2009).*
Zellkraftwerk. Zellkraftwerk: Next Generation Cytometry (Apr. 5, 2016).*
European Search Report based on application No. 16189483.7 (10 pages) dated Mar. 20, 2017 (Reference Purpose Only).
Christian Hennig et al., "A Versatile Platform for Comprehensive Chip-Based Explorative Cytometry", Cytometry Part A, 2009, pp. 362-370, vol. 75A, No. 4, ISAC.
Zellkraftwerk, "Next Generation Cytometry", retrieved Jan. 20, 2017, from https://web.archive.org/web/20160405094646/http://zellkraftwerk.com/Technology.phtml.
Jelena Skuljec et al., "Monocyte/macrophage lineage commitment and distribution are affected by the lack of regulatory T cells in scurfy mice", European Journal of Immunology, 2016, pp. 1656-1668, vol. 46, WILEY-VCH Verlag GmbH & Co. KGaA, Weinheim.
Charles A. Smith et al., "A Simple Correction for Cell Autofluorescence for Multiparameter Cell-based Analysis of Human Solid Tumors", Cytometry Part B (Clinical Cytometry), 2006, pp. 91-103, vol. 70B, No. 2, International Society for Analytical Cytology.
Mario Roederer et al., "Cell-by-Cell autofluorescence Correction for Low Signal-to-Noise Systems: Application to Epidermal Growth Factor Endocytosis by 3T3 Fibroblasts", Cytometry, 1986, pp. 558-565, vol. 7, No. 6.
Gratama, Jan W. et al; Flow Cytometric Enumeration of CD341 Hematopoietic Stem and Progenitor Cells; Cytometry (Communications in Clinical Cytometry) 34; 1998; pp. 128-142; European Working Group on Clinical Cell Analysis.
European Search Report based on Application No. 20186057.4 (11 Pages) dated Aug. 14, 2020.

* cited by examiner

*Primary Examiner* — Gailene Gabel
(74) *Attorney, Agent, or Firm* — Lewis Rice LLC (57) ABSTRACT

Methods for single cell analysis by determining the presence and/or amount of one or more target molecules in a plurality of cells may include: (i) immobilizing said plurality of cells on a solid substrate, wherein the cells are immobilized in form of a monolayer; (ii) determining the position of the individual immobilized cells on the solid substrate; (iii) measuring the auto-fluorescence of the individual immobilized cells; (iv) contacting the immobilized cells with a first detection reagent comprising (a) a moiety that specifically recognizes and binds a first target molecule and (b) a fluorescent label under conditions that allow binding of the detection reagent to the first target molecule; (v) measuring the fluorescence of the fluorescent label of the detection reagent bound to the first target molecule for the individual immobilized cells; (vi) determining the presence and/or amount of the first target molecule in the individual immobilized cells by comparing the fluorescence measured in step (v) with the fluorescence measured in step (iii) on a cell-by-cell basis.

19 Claims, 3 Drawing Sheets

FIG. 2B

METHOD OF DETERMINING THE PRESENCE AND/OR AMOUNT OF TARGET MOLECULES

CROSS-REFERENCE TO RELATED APPLICATIONS

The present application claims priority to European Patent Application No. 16 189483.7, filed on Sep. 19, 2016, which is herein incorporated by reference in its entirety.

TECHNICAL FIELD

The subject matter herein generally lies in the field of cell biology and relates to methods for single cell analysis by determining the presence and/or amount of one or more target molecules in a plurality of cells.

BACKGROUND

Flow cytometers and fluorescence-activated cell sorters (FACS) are currently the gold standard for the characterization of cells in suspension using fluorescent antibodies and other dye-tagged probes. They are widely used analytic tools in biomedical research and clinical diagnostics and greatly facilitate the study of both physical properties (e.g., size, shape) and biochemical properties (e.g., cell cycle distribution, DNA contents) of biological samples, such as cells. Information about the cells of interest is obtained optically in a nondestructive and quantitative manner (Givan, A., 2001, Flow Cytometry: First Principles, John Wiley & Sons, New York). Flow cytometry is commonly used in a variety of biomedical fields (for example, immunology or cellular and molecular biology), allowing studies of cell cycle analysis, gene expression levels, intracellular cytokine measurement, vaccine analysis, phagocytosis, and much more (Shapiro, H. and Leif, R., 2003, Practical Flow Cytometry, Wiley-Liss, New York). Besides its applications in basic biomedical research, flow cytometry has become an important clinical tool to monitor the progression of hematological diseases such as leukemia and AIDS. Modern FACS systems can optically screen tens of thousands of cells per second and then sort out a specific subpopulation of cells for further analysis, enabling studies of rare samples, such as stem cells (Gratama J., et al., 1998, Cytometry 34, 128).

Traditional flow cytometry detects and analyzes optical signals (angular light scatter or emitted fluorescence) to identify individual cells or biological samples. For the case of fluorescent signal detection, the measured signal consists of background noise, autofluorescence of the cell, the signal of non-specifically bound fluorescence markers and finally the signal of specifically bound markers attached to target molecules on or in the cells (provided that the measurement is carried out in the dynamic range of the FACS device). For determining the desired result only the signal of the specifically bound markers is of relevance, while the rest of the measured signal is "noise" or so-called error of measurement. This error prevents that the specific signal can be measured more sensitively and in cases of a low intensity of the specific signal and a relatively high intensity of the background, the specific signal may "disappear" in the background leading to the false negative results. The background signal therefore directly influences the detection sensitivity of the flow cytometry measurement. Further, the background signal also influences the distinction between positive and negative samples/cell populations, as the measured positive and negative values may become indistinguishable dependent on the background signal.

The main reasons for measurement errors are a high background signal and a small dynamic range of the detection device, high autofluorescence signals of the cells, unspecific binding of the markers to the cell and variations that occur during the staining process (e.g. different marker concentrations, labeling of the marker or staining conditions). While it is desirable to reduce the unspecific background signals as much as possible, FACS-based methods have only limited potential to reduce background signals. In principle, it is only possible to reduce the basic background signal of the FACS device by providing a broad dynamic measurement range and by avoiding the accumulation of interfering signals.

In order to eliminate the background signal of the detection device and the autofluorescence of the cells, currently known methods typically use a control sample in which the investigated cells are not treated with the fluorescence detection reagent. However, this approach has a number of drawbacks, as by comparing two different populations of cells further measurement errors may occur. This is due to the fact that the populations may differ in their density, age, expression intensity of the investigated marker, etc. Further, also the fluorescence of the sample material (aside from the cells) may vary between different samples due to variations in their manufacturing processes or their compositions. Finally, and most significantly, the control sample value is typically an average value that is calculated on the basis of a control sample measurement and does not take into consideration the variations that exist between individual cells. This leads to the situation that cells having a low autofluorescence and cells having a high autofluorescence are calibrated against the same average control sample value, with the result that cells having a low autofluorescence are prone to be evaluated as (false) negatives and cells having a high autofluorescence are likely to be evaluated as (false) positives. As all the above can significantly impair sensitivity of the detection method, it would be desirable to have methods available that overcome the drawbacks of existing methods and allow a more sensitive and reliable cell analysis.

SUMMARY

It is an object of the present invention to meet the above need for a more sensitive and reliable cell analysis method by providing methods for single cell analysis that include determining the presence and/or amount of one or more target molecules in a population of a plurality of cells. The method(s) are based on the principle that intact cells are immobilized on a solid substrate and that the position of each individual cell on the solid substrate is (e.g. automatically) determined to allow identification of the cell and (e.g. fluorescence) signal determination for a single cell in more than one cycle of signal detection. This makes it possible to use a single cell immobilized on the solid substrate for at least two fluorescence measurements, with the first measurement being done before the cell is contacted with a detection reagent, for example a fluorescent label-tagged antibody. This first measurement provides a background signal value for the individual cell, such as its autofluorescence, and also includes the basic background signal of the used detection device, the substrate, etc. In a second measurement step, the cell is first contacted with the detection reagent that binds to a given target molecule. Based on the previously determined position of the cell on the solid substrate, the cell may be identified and the measured signal calibrated against the individual background signal value obtained in the first measurement, for example by simply subtracting the value of the first fluorescence measurement from the value of the second measurement. This allows a single cell analysis where each individual cell signal is calibrated against its own individual background signal and thus allows a significant reduction of the measurement errors typically observed in existing methods. Hence, the method (s) provide improved fluorescence detection signals by decreasing the background signal on an individual cell basis.

The method(s) are therefore directed to a method for single cell analysis by determining the presence and/or amount of one or more target molecules in a plurality of cells, comprising: (i) immobilizing the plurality of cells on a solid substrate, wherein the cells are immobilized in a monolayer form, which may be optionally spaced apart from each other in a non-limiting embodiment; (ii) determining the position of the individual immobilized cells on the solid substrate; (iii) measuring the auto-fluorescence of the individual immobilized cells; (iv) contacting the immobilized cells with a first detection reagent comprising (a) a moiety that specifically recognizes and binds a first target molecule and (b) a fluorescent label under conditions that allow binding of the detection reagent to the first target molecule; (v) measuring the fluorescence of the fluorescent label of the detection reagent bound to the first target molecule for the individual immobilized cells; (vi) determining the presence and/or amount of the first target molecule in the individual immobilized cells by comparing the fluorescence measured in step (v) with the fluorescence measured in step (iii) on a cell-by-cell basis; (vii) optionally repeating steps (iv) to (vi) with a second or further detection reagent comprising (a) a moiety that specifically recognizes and binds a second or further target molecule and (b) a fluorescent label.

BRIEF DESCRIPTION OF THE DRAWINGS

The invention will be better understood with reference to the detailed description when considered in conjunction with the non-limiting examples and the accompanying drawing.

DETAILED DESCRIPTION

The present inventors have developed methods that allow analysis of a plurality of cells on a cell-by-cell basis with an increased sensitivity. The analysis is typically achieved by the detection of fluorescent signals from given target molecules on a cell, with the fluorescent signals measured being less prone to errors from background noise and cellular autofluorescence. As already described above, the increased sensitivity is achieved by a reduction of the background and the cells' autofluorescence by two separate fluorescent measurements of the same cell. The first measurement of the cells is made before the cells are contacted with a detection reagent, such as a fluorescently labeled antibody, to determine each individual cell's fluorescence in the absence of a detection reagent. Either simultaneously with this first measurement or even prior to it, the position of each of the analyzed cells on a solid support, on which they are immobilized, is determined and the positional data is stored for subsequent measurements. The second measurement is made after the cells have been contacted with the detection reagent. As the position of each individual cell as well as its fluorescent signal in the absence of the detection reagent has been recorded prior to the second measurement, the value measured with this second measurement can be corrected by each individual cell's innate fluorescence and the background at the cell's position, thus obtaining a more specific signal for each cell. In other words, as the first and the second measurements are taken for each cell independently, the calculated values represent individually corrected data. This is highly advantageous as it avoids a calibration of the cellular fluorescence by a correction factor that has been determined based on a different cell or sample and usually represents an average value determined based on a population of cells different from the analyzed cell. Further, as the cells are immobilized and their position is recorded, they can be subjected to multiple cycles of detection, for example of different markers, so that a much more specific cellular marker profile can be generated for each individual cell. This greatly improves the possibility for a reliable single cell analysis, as it takes into account that even within a population of cells of the same cell type, significant variations with respect to autofluorescence and marker expression may exist. Accordingly, errors or false results that arise from using not the same cell for reference measurements and testing can be avoided.

Thus, in a first non-limiting embodiment, a method for single cell analysis may include determining the presence and/or amount of one or more target molecules in a plurality of cells, comprising: (i) immobilizing said plurality of cells on a solid substrate, wherein the cells are immobilized in form of a monolayer and may be optionally spaced apart from each other; (ii) determining the position of the individual immobilized cells on the solid substrate; (iii) measuring the auto-fluorescence of the individual immobilized cells; (iv) contacting the immobilized cells with a first detection reagent comprising (a) a moiety that specifically recognizes and binds a first target molecule and (b) a fluorescent label under conditions that allow binding of the detection reagent to the first target molecule; (v) measuring the fluorescence of the fluorescent label of the detection reagent bound to the first target molecule for the individual immobilized cells; (vi) determining the presence and/or amount of the first target molecule in the individual immobilized cells by comparing the fluorescence measured in step (v) with the fluorescence measured in step (iii) on a cell-by-cell basis; (vii) optionally repeating steps (iv) to (vi) with a second or further detection reagent comprising (a) a moiety that specifically recognizes and binds a second or further target molecule and (b) a fluorescent label.

The term "single cell analysis", as used herein, refers to analyzing individual cells in a sample containing a plurality of cells, for example by testing each individual cell for the presence or absence or the amount of a given marker molecule. The analysis can be example be done by using labeled detection reagents specific for a marker molecule of interest that are contacted with the cell under conditions that allow binding of the detection reagent to the marker molecule and then determining the presence and the amount of the bound detection reagent by means of the label. Commonly used detection methods involve the use of fluorescently labeled detection reagents and measuring the fluorescence of the bound label.

"Determining the presence", as used herein, is directed to a qualitative analysis, typically by setting a threshold value for the determined signal, which when met or exceeded is considered to be indicative for the presence of a molecule of interest. Signal values below the threshold value are accordingly considered to be indicative for the absence of the molecule of interest. Similarly, the term "determining the amount", as used herein, refers to a quantitative analysis, wherein the strength of the signal is determined, with the signal strength corresponding to the local concentration of the marker molecule. For example, these quantitative results may be relative fluorescent units that have been measured by determining the fluorescence signal of fluorescent labels bound to a given target molecule.

"Target molecule", as used herein, refers to a biological molecule that is either naturally present in or on a cell or has been artificially introduced into or onto a cell. A "target molecule" can be any molecule, typically organic molecule, such as a peptide, including oligo- and polypeptides as well as proteins, lipid, nucleic acid, small molecule, or carbohydrate as well as hybrids of the afore-mentioned molecules, such as glycosylated proteins. The target molecule may be located within the cell, for example in the nucleus, nucleolus, cytoplasm, mitochondria, Golgi apparatus, or endoplasmic reticulum, or may be located in or on the cell membrane. In various non-limiting embodiments, the target molecules, the presence and/or amount of which is determined in the methods, may be polypeptides. In various non-limiting embodiments, the target molecule is a cell surface molecule, i.e. a molecule attached to or inserted into an outer side of a cell membrane and is at least partially exposed to the cellular surrounding.

In various non-limiting embodiments, the "target molecule" is a "biomarker", "marker molecule" or "marker". The terms "biomarker", "marker molecule" and "marker", as used interchangeably herein, generally refer to a molecule the presence or amount of which can be determined and has informational value in that it is indicative for a cell type, cell condition, cell stage, etc. Said information may then in turn be indicative or predictive for a condition or state of the organism from which the cell was obtained.

As used herein, the terms "polypeptide", "protein", "peptide" refer to a polymeric form of amino acids of any length, which can include coded and non-coded amino acids, chemically or biochemically modified or derivatized amino acids, and polypeptides having modified peptide backbones. Throughout the application, the standard one letter notation of amino acids will be used. Typically, the term "amino acid" will refer to "proteinogenic amino acid", i.e. those amino acids that are naturally present in proteins. Most particularly, the amino acids are in the L isomeric form, but D amino acids are also envisaged. Polypeptide molecules useful as target molecules typically comprise at least 20, at least 50, at least 100, at least 150, at least 200, at least 300 or at least 500 amino acids.

Suitability of target(s) to be analyzed may be determined by the type and nature of analysis required for the biological sample. In some embodiments, a target may provide information about the presence or absence of an analyte in the biological sample. In another embodiment, a target may provide information on a state of a biological sample. For example, the methods disclosed herein may be used to detect target(s) that may help in comparing different types of cells or tissues, comparing different developmental stages, detecting the presence of a disease or abnormality, or determining the type of disease or abnormality.

Suitable targets have already been listed above and include one or more of peptides, proteins, such as antigens, enzymes and receptors, nucleic acids (e.g., polynucleotides, DNA, RNA, or aptamers), polysaccharides (e.g., lectins or sugars), and lipids. One or more of the aforementioned targets may be characteristic for a particular cell type, while other targets may be associated with a specific disease or condition. In some embodiments, targets in a cell sample that may be detected and analyzed using the methods disclosed herein may include, but are not limited to, cell surface proteins, such as receptors, for example receptors for hormones or growth factors, and ligands, in particular the CD (cluster of differentiation) family of cell surface molecules, commonly used for immunophenotyping of cells.

Examples of hormone or hormone receptor targets, include, but are not limited to, human chorionic gonadotropin (HCG), adrenocorticotropic hormone, carcinoembryonic antigen (CEA), prostate-specific antigen (PSA), estrogen receptor, progesterone receptor, androgen receptor, gC1q-R/p33 complement receptor, IL-2 receptor, p75 neurotrophin receptor, PTH receptor, thyroid hormone receptor, and insulin receptor.

Examples of hematopoietic cell targets include, but are not limited to, CD45, CD34, CD133, HLA-DR, CD115, CD116, CD117, CD33, CD38, CD90, CD71, Ki67, Flt3, CD163, CD45RA, CD3, IgD, CD105, CD45, and c-kit.

Examples of lymphoid cell targets include, but are not limited to, alpha-1-antichymotrypsin, alpha-1-antitrypsin, CD19, CD20, bcl-2, bcl-6, BLA 36 (B lymphocyte antigen 36 kD), BMI (myeloid target), BM2 (myeloid target), galectin-3, granzyme B, HLA class I Antigen, HLA class II (DP) antigen, HLA class II (DQ) antigen, and HLA class II (DR) antigen.

Examples of CD markers include, but are not limited to, CD1a, CD1b, CD1c, CD1d, CD1e, CD2, CD3delta, CD3epsilon, CD3gamma, CD4, CD5, CD6, CD7, CD8alpha, CD8beta, CD9, CD10, CD11a, CD11b, CD11c, CDw12, CD13, CD14, CD15, CD15s, CD16a, CD16b, CDw17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44R, CD45, CD46, CD47, CD48, CD49a, CD49b, CD49c, CD49d, CD49e, CD49f, CD50, CD51, CD52, CD53, CD54, CD55, CD56, CD57, CD58, CD59, CDw60, CD61, CD62E, CD62L, CD62P, CD63, CD64, CD65, CD65s, CD66a, CD66b, CD66c, CD66d, CD66e, CD66f, CD68, CD69, CD70, CD71, CD72, CD73, CD74, CDw75, CDw76, CD77, CD79a, CD79b, CD80, CD81, CD82, CD83, CD84, CD85, CD86, CD87, CD88, CD89, CD90, CD91, CDw92, CDw93, CD94, CD95, CD96, CD97, CD98, CD99, CD100, CD101, CD102, CD103, CD104, CD105, CD106, CD107a, CD107b, CDw108, CD109, CD114, CD115, CD116, CD117, CDw119, CD120a, CD120b, CD121a, CDw121b, CD122, CD123, CD124, CDw125, CD126, CD127, CDw128a, CDw128b, CD130, CDw131, CD132, CD134, CD135, CDw136, CDw137, CD138, CD139, CD140a, CD140b, CD141, CD142, CD143, CD144, CDw145, CD146, CD147, CD148, CDw149, CDw150, CD151, CD152, CD153, CD154, CD155, CD156, CD157, CD158a, CD158b, CD161, CD162, CD163, CD164, CD165, CD166, and TCR-zeta.

"Plurality of cells", as used herein, means that more than one, namely at least 2, 3, 4, 5, 6, 7, 8, 9 or 10 cells are concerned. In various embodiments, a plurality of cells comprises at least 30, 50, 80, 100, 200, 500 or 1000 cells. In various non-limiting embodiments, the cells are eukaryotic cells that are analyzed in the methods. The eukaryotic cells may be hematopoetic cells in a non-limiting embodiment. The hematopoietic cells may be or include, but are not limited to, myeloid cells (e.g. erythrocytes, thrombocytes, neutrophils, monocytes and macrophages, eosinophils, basophils, mast cells, or combinations thereof), lymphoid cells (e.g. B-cells, various types of T-cells, NK-cells, or combinations thereof), or combinations thereof. The cells that do not produce hemoglobin may be referred to as leukocytes. The cells that produce hemoglobin (red blood cells) may be referred to as erythrocytes. A collective term for cells involved in immune response is lymphocytes.

The term "immobilizing", as used herein, means that cells are fixated to a given substrate such that they can no longer move freely and more specifically cannot move from the position at which they are immobilized. The immobilization may be achieved by binding the cells specifically or non-specifically to the solid substrate. In this regard the term "non-specifically" means that the material which binds the cells binds the cells without any distinction, i.e. without any form of purposive selection. Such unspecific immobilization may be achieved by a number of different strategies all of which are well-known to those skilled in the art. In various embodiments, the methods described herein use non-specific immobilization, such as non-covalent non-specific immobilization. Such immobilization may, for example, be mediated by electrostatic interactions, van der Walls forces or hydrogen bonding. In non-limiting embodiments, as will be described below, immobilization is achieved by coating the substrate with negatively charged molecules that then bind the predominantly positively charged cells by electrostatic interactions.

In contrast, "specific immobilization" is a form of immobilization that is cell- or cell type-specific. This may be achieved by coating a substrate with a capture reagent that has specificity for a certain type of cell, such as antibodies. In this context, a "cell type" is defined as cells that can be distinguished from other cells by their morphology or phenotype.

Generally, the immobilization is optionally achieved by means that allow the cells to maintain their essentially spherical or elliptical form in suspension upon immobilization, i.e. essentially without the often observed "flattening" of the cell shape. This is advantageous for the following steps of cell position determination and imaging. The techniques described herein for cell immobilization all allow maintaining the cells in their essentially spherical or elliptical form.

As used herein, the term "solid substrate" means a substrate that is solid under standard conditions (temperature of about 20° C. and pressure of about 1013 mbar). The solid substrate may be have any shape, including substrates having at least one substantially flat surface (for example, "slide"-, "membrane"- or "chip"-shaped substrates) and substrates having a curved surface (for example, bead-shaped substrates and tube-shaped substrates). Those of skill in the art will be familiar with the variety of materials, shapes and sizes of solid substrates that are routinely used in the art. Typically, the solid substrates used are suitable for immobilizing cells and include any solid substrate known in the art to be suitable for such purposes. Non-limiting examples, without limitation, include slides, vials, tubes, cartridges, or combinations thereof.

The substrate material may be any suitable material, with the most common ones being glass and plastics, such as polypropylene, polycarbonate, polyacrylate, PET, and the like. It is understood that the support material is suitable for the detection method. For example, for fluorescence detection, it is typically required that the substrate material is transmissive for light of a given wavelength to allow excitation of the label and detection of the emitted fluorescence.

The term "monolayer", as used herein, refers to a layer of cells in which essentially no cell is positioned on top of another. In various embodiments, this means that the cells are 2-dimensionally spread out on a (typically planar) surface. As immobilization is typically achieved via interaction with the solid substrate, monolayer formation may be achieved by blocking or inhibiting cell-cell interactions, while at the same time promoting cell-surface interactions. "Spaced apart from each other", as used herein, means that individual cells being immobilized on the same surface do not directly contact each other. The distance between two cells can be expressed in x times the average diameter of the cells, for essentially round cells, or the average extension in the largest dimension, in case of elongated cell shapes. In various embodiments, the distance between two cells is at least 0.1, 0.2, 0.3, 0.5 or 1.0 times the average diameter or average extension. The spacing of cells immobilized on a substrate can be influenced by the cell concentration in the sample contacted with the substrate. In various embodiments, samples are therefore diluted such that they contain at most $10^8$, $10^7$, $10^6$, $10^5$, $10^4$, $10^3$, or $10^2$ cells per milliliter (mL). The monolayer orientation, as well as the spacing of the cells, allows determination and recording of the position of each individual cell.

"Determining the position", as used herein, refers to a process in which the position of individual cells immobilized on a solid support is determined relative to a reference point on the solid support or relative to each other. In a non-limiting embodiment, this process may be automated and relies on a computer program that can recognize cells and assigns a positional identifier to each cell. Once this process is complete, the positional information is recorded so that each cell may be clearly identified at any time when the solid support is analyzed. As the positional information is recorded relative to a reference point or relative to all other cells, each individual cell can be readily re-identified even if the solid support is turned, flipped, etc. This allows analysis of the same individual cell multiple times. In various embodiments, the determination of the position is based on an initial picture that is taken of a given population of immobilized cells. This initial picture is used as a reference in further measurements of the same population of cells. In various embodiments, computer software programs can match the same cell in the initial picture and further pictures. As noted above, either a reference point on the solid substrate or the relative positions of the cells with respect to each other are used for re-identification of each cell. The positional date may be stored on a data storage medium, such that it is easily retrieved for later measurements. Software and devices that allow the determination, storage and retrieval of positional information of cultured cells are commercially available. In various embodiments, without further limitation, the device used for position determination of the cells is a computer-assisted microscope stage. The positional information can for example be stored by determining/calculating the coordinates, e.g. x/y coordinates, of each cell's center and storing said coordinate data as well as the cell size.

In various embodiments, the cell positioning is determined in an automated fashion using a light microscope in transmission mode. To achieve this, first the focal plane is determined, followed by recording at least two images of each cell, wherein one image may be taken in the focal plane and the other slightly off-focus or both are taken off-focus. In various embodiments, several images that are slightly off-focus are recorded. Typical ranges for off-focus images range from the focal plane ±100 µm. In has been found to be particularly advantageous, if two or more images are taken slightly off-focus, for example a first image in a plane that is close to the focal plane, e.g. ±5 or ±10 µm, and a second image that is farther away from the focal plane, e.g. ±20-50 µm. In one embodiment, the first image is taken +5 µm off-focus and the second +40 µm off-focus. In another embodiment, the first image is taken −1 µm off-focus and the second +10 µm off-focus. Generally, this technique is advantageous, as the off-focus images sharpen the cell's outline. By overlaying said images the round shapes of individual cells can be easily identified in an automated fashion by using a specifically adapted computer software program. Said specific method of identifying cells and recording their position in an automated fashion by light (transmission) microscopy, using two or more images of the same setup of cells immobilized on a solid support recorded in different (off-)focus planes, with one image recorded in the focal plane and the other image(s) recorded slightly off-focus or both recorded slightly off-focus, and then overlaying said images for identifying cellular shapes and thus determining the position of the individual cells relative to a reference point or to each other in another non-limiting embodiment. While this technique is used herein in connection with fluorescence microscopy for target detection, it is understood that its use is not limited thereto, but can be readily expanded to other techniques where position recording of immobilized cells is useful or necessary.

The term "measurement" or "measuring", as interchangeably used herein, relates to the determination of a signal, typically including quantification of detected signals. The measured signals are fluorescence signals in a non-limiting embodiment. The fluorescence signal measured includes the auto-fluorescence of the cells, the background fluorescence, if any, and, depending on the step, the actual detection reagent fluorescence. The term "auto-fluorescence", as used herein, relates to the natural fluorescence of cells and cellular biological structures, such as mitochondria, lysosomes and other cell organelles, and is used to distinguish this innate fluorescence of the cell from the fluorescence originating from artificially added fluorescent markers (fluorophores). As the auto-fluorescence and the marker fluorescence are measured for each cell individually, it is possible to correct signals on an individual cell level and thus achieve a much more sensitive and reliable measurement.

"Contacting", as used herein, refers generally to providing access of one component, reagent, analyte or sample to another and includes dissolving, mixing, slurrying, stirring, or combinations thereof.

By the term "detection reagent", as used herein, is meant any molecule, or complex of molecules, with a specific binding affinity for an analyte of interest that allows detection thereof by a given detection method. In some embodiments, the detection reagent may be a conjugate of a target-binding moiety and a label, such as a fluorescent dye or fluorophore. The detection reagent is used to detect the presence or absence of a target molecule. Detection reagents, in particular the target-binding moieties thereof, include, but are not limited to, nucleic acids, nucleic acid sensor molecules, aptamers, antibodies, combinatorial peptides, combinatorial proteins, and small molecules. In various embodiments, the detection reagent is an antibody conjugated to a label, such as a fluorophore. By "fluorescent detection reagent", as used herein, is meant any detection reagent which possesses fluorescent properties in that either the target-binding moiety itself is fluorescent or in that it is conjugated to a fluorescent dye. Depending on the molecular structure of the detection reagent, fluorescent dyes may be conjugated to the target-binding part by different functional groups. Suitable functional groups for conjugation include, but are not limited to, amino groups, carboxy groups, maleimide groups, oxo groups and thiol groups. For example, fluorescent dyes containing amino groups can be attached to detection reagents containing amino groups using cross-linkers known in the art.

The detection reagent may be specific for a given target. "Specific", as used in this context, means that it binds to the target over other non-target molecules. The binding may occur with at least 10fold, such as at least 100fold, or at least 1000fold higher affinity, as for example measured by $K_d$, to its target compared to other structurally unrelated molecules that may also be present in the sample or the cell, but does not necessarily mean that the affinity is high. However, the affinity of the detection reagent for the target is high enough to allow detection under measurement conditions. This may for example mean that the affinity ($K_d$) of the detection reagent for the target is 1 µM or lower, such as 0.1 µM or lower, or 10 nM or lower, as for example determined by isothermal titration calorimetry, surface plasmon resonance or other suitable methods for affinity measurements.

Fluorophores useful as fluorescent labels can be either "small molecule" fluorophores or proteinaceous fluorophores (e.g. green fluorescent proteins and all variants thereof). Suitable small molecule fluorophores include, but are not limited to, 4',6-Diamidino-2-phenylindole (DAPI), BODIPY FL, Coumarin, Cy5, Dansyl glycine, EDANS, Fluorescein, TAMRA, Texas Red® (TR). Suitable optical dyes are well-known in the art and are, for example, described in the 1996 Molecular Probes Handbook by Richard P. Haugland.

In various embodiments, the fluorescent dye may be a fluorescent protein such as green fluorescent protein (GFP; Chalfie, et al., Science 263(5148):802-805 (Feb. 11, 1994); and EGFP; Clontech—Genbank Accession Number U55762), blue fluorescent protein (BFP; 1. Quantum Biotechnologies, Inc. 1801 de Maisonneuve Blvd. West, 8th Floor, Montreal (Quebec) Canada H3H 1J9; 2. Stauber, R. H. Biotechniques 24(3):462-471 (1998); 3. Heim, R. and Tsien, R. Y. Curr. Biol. 6:178-182 (1996)), cyan fluorescent protein (CFP), and enhanced yellow fluorescent protein (EYFP; 1. Clontech Laboratories, Inc., 1020 East Meadow Circle, Palo Alto, Calif. 94303).

In various other embodiments, the fluorescent dye may be a fluorescent semiconductor nanocrystal particle, or quantum dot, such as those obtainable from Life Technologies Corporation (Carlsbad, USA).

As detailed above, in various embodiments, fluorescent molecules (fluorophores) can be conjugated to target-binding moieties to form detection reagents. The fluorophores can be activated (excited) by light from a detection instrument and emit light of a different wavelength. Since the detection reagents bind to targets on or in the cells, the amount of light detected from the fluorophores corresponds to the number of targets in or on a given cell.

Depending on the type of detection reagents used, it may be possible to use several detection reagents, for example several fluorescent detection reagents, simultaneously, in that the cells are contacted with these detection reagents simultaneously or successively and then the different detection reagents are separately detected, for example in case different fluorophores are used for the different detection reagents, by measuring fluorescence at different wavelengths. The labels of the different detection reagents may be sufficiently different so to allow distinction upon measuring their respective signals. In case of fluorophores this may mean that their peak emittance is sufficiently different from the other fluorophores used.

The term "comparing the fluorescence", as used herein, refers to the comparison of the fluorescence of a given cell determined before the cells have been treated with the detection reagent (i.e. their auto-fluorescence and background fluorescence) and the fluorescence data determined in the measurements of the same cell with said cell having been contacted with a detection reagent. The comparing may occur, in an automated fashion in a non-limiting embodiment, in that the determined auto-fluorescence of the respective cell and the background signal are subtracted from the actual measurement value to provide a corrected value that is representative for the amount of detection reagent bound to said cell and thus in turn representative for the amount/concentration of target molecules present on or in said cell. The comparison can be carried out pixel-wise, i.e. by pixel-wise subtraction of the fluorescence values. Alternatively, for each fluorescent image the respective fluorescence values may first be calculated and then subtracted from each other. Accordingly, the term "cell-by-cell basis", as used herein, refers to this individually calculated fluorescence of a given cell that has been corrected by its own individual auto-fluorescence and background.

It is important to note that said comparison of the fluorescence values obtained for the cells' autofluorescence and those obtained from the actual fluorescence microscopy imaging of the target markers to be analyzed is clearly distinct from previously disclosed method of a local background correction that does not specifically compare the cells' fluorescence before and after staining as well as techniques that use multiple images for correcting local imhomogeneity of illumination.

However, the present embodiments, wherein inhomogeneities of illumination are corrected within one measurement, for example the background measurement, the actual (marker) measurement or both, by normalizing the individual values (positions) in one setup against each other, typically against the first value (position) determined. Thus, an image that has already been corrected for illumination inhomogeneities is obtained in each of both setups, i.e. the determination of autofluorescence and the actual fluorescence measurement, and can then be used as described above.

The fluorescence data for each cell can be recorded and stored together with the positional information. For example, it is possible to store said data in a list-mode format. For further analysis a multivariate gating can be performed manually and/or each cell can be grouped by hierarchical clustering, with the resulting groups being then compared with a model-cytometry-ontology for the purpose of cell identification, knowledge capture and structuring.

In various embodiments, the method further comprises a step of bleaching the detection reagent, quenching the signal of the detection reagent, or removing the detection reagent after step (vi) and prior to the next detection cycle. "Bleaching" or "photobleaching", as interchangeably used herein, refers to the photochemical alteration of a label, typically a dye or a fluorophore molecule, such that it permanently loses its ability to provide a detectable signal, e.g. to fluoresce. This may be achieved by exposure to light of a defined wavelength and intensity for a period of time sufficient to photobleach the label. Other options to inactivate the label are cleaving the bond between the target-binding moiety and the label or inhibiting the label's signaling properties by use of an inhibitor, such as a quencher molecule.

Photobleaching may also be used prior to the step of contacting the cells with the detection reagent, for example to quench autofluorescence. This can help to improve signal-to-noise ratio. This is either done before auto-fluorescence is determined or the auto-fluorescence measurement is repeated prior to the actual detection reagent measurement. In various embodiments, the photobleaching is carried out with a laser.

"Quenching", as used herein, refers to any process which decreases the fluorescence intensity of a given substance. A variety of processes can result in quenching, such as excited state reactions, energy transfer, complex-formation and collisional quenching. As a consequence, quenching is often heavily dependent on pressure and temperature. Molecular oxygen, iodide ions and acrylamide are common chemical quenchers.

In various embodiments, the detection reagents are removed before the next detection cycle. This generally means that the detection molecule is released from its target molecule. The release may be achieved by a plurality of washing cycles, out-titration of the detection molecule with detection molecule binding agents that compete for the target binding or a combination of both, washing and out-titration. Alternatively, if the detection molecule is a conjugate of a target-binding part and a label, the label may be cleaved off from the rest of the molecule. Suitable cleavable antibody conjugates are well-known in the art, and are for example described in international patent publication WO2010/070037.

As already described above, in various embodiments, the method comprises a step of bleaching the immobilized cells prior to steps (iii)-(vii) to reduce auto-fluorescence of the cells.

In various embodiments, steps (iv) to (vi) are repeated 1-50 times, such as 2-20 times, or 4-10 times. In each of these cycles, a detection reagent with specificity for a different marker may be used, such that each cell is characterized with respect to a panel of markers that are detected and quantified. This allows, for example, immunophenotyping individual cells. The advantage of such a method compared to known FACS methods is that the same cell is analyzed for the presence and concentration of different markers and that the number of markers that can be determined is in principle not limited as the measurement does not need to be simultaneously (by use of different labels and channels) but can be done successively. It is even possible to store the substrate with the immobilized cells after a measurement and repeat the same measurement or perform other measurements at a later time. This is a further important advantage over existing FACS techniques where the cells are typically discarded after one measurement cycle and no identification of an individual cell is possible after the measurement.

In various embodiments, the cells are non-specifically immobilized on a solid substrate, such as by functionalizing the solid substrate surface with negatively charged functional groups, before contacting a cell-containing sample with the functionalized solid substrate surface. This may be achieved by chemical or physical treatment of the surface to alter its chemistry. In one non-limiting embodiment, acids or bases are used for such modification. In one embodiment, where the substrate is a glass substrate, the substrate is first treated with hydrofluoric acid (HF) and then with an alcohol, such as ethanol. It is possible to carry out several washing steps before, between and after the functionalization steps, such as with water or a suitable buffer. It has been found that a substrate surface such treated can immobilize cells very efficiently and at the same time allows the cells to maintain the spherical or elliptical form, i.e. essentially without flattening of the cells. Alternatively, the solid substrate surface may be functionalized with a suitable cell-binding molecule, such as an anionic biomolecule or polymer, and contacting a cell-containing sample with the functionalized solid substrate surface. The term "cell-binding molecule", as used herein, refers to molecules that are able to attach to the surface of a cell. These molecules can bind, without limitation, to cell membrane proteins, carbohydrates that modify membrane proteins, other molecules that modify membrane proteins or the lipid membrane itself. Cell adhesion, meaning the binding of a cell to a surface or substrate, may be mediated by so-called cell adhesion molecules. Examples of these protein molecules include selectins, integrins, and cadherins. In non-limiting embodiments, the cell-binding molecules are anionic biomolecules or polymers. The anionic biomolecules/polymers used in the methods are nucleic acids, such as DNA. Thus, in various embodiments, the solid substrate surface is functionalized with DNA molecules. It is to be noted that the actual base composition of the nucleic acid molecule is of essentially no importance for the desired functionality, rather the binding ability is dependent on its general structure and the negative net charge. DNA molecules have a random or arbitrary base sequence and a length of at least 5, 10, 15, 20, 30, 50, 100, 150 or 200 bases. However, to avoid formation of secondary structures, it may be necessary to use homopolymers of only one type of nucleotide. In some embodiments, the DNA molecules may be modified, for example in their backbone. Such modifications may serve the purpose to increase stability of the DNA molecules or increase the net charge thereof.

In various embodiments, the solid substrate is at least partially optically transmissive for light of the excitation and/or emission wavelength to allow excitation of the fluorophore and detection of the emitted light. "Partially optically transmissive" therefore means that a defined part of the solid substrate on which the cells are immobilized is sufficiently transmissive for light of the relevant wavelength to allow fluorescence measurements.

In various embodiments, the solid support is part of a device that is at least partially optically transmissive to allow fluorescence detection and has an inlet and outlet to allow passage of a fluid medium therethrough. The device may be a device as described in international patent publication WO 2010/049430 A1 in a non-limiting embodiment. The device may have the form of a closed cartridge that has said inlet and outlet openings for loading of the cells, contacting with the detection reagent, various washing steps and the like. In various embodiments, the solid support is a substantially flat carrier substrate that forms a channel together with two spacer elements arranged on the carrier substrate and a top coating that extends parallel to the carrier substrate is spaced apart therefrom by means of the spacer elements. All these elements may be connected (permanently fixed) to each other and parts of the carrier substrate and the top coating being parallel to each other may be optically transmissive to allow analysis of the cells immobilized on the carrier substrate. The spacer elements may be designed and arranged such that they define a channel that connects at least one inlet and at least one outlet opening, with the inlet and/or outlet each being arranged in the carrier substrate or the top coating or between both in a spacer element. The channel may have the same diameter as the inlet and/or outlet opening at its ends with the diameter increasing from each end towards the middle between inlet and outlet to allow bubble-free flow of a liquid sample or medium into and through the "cartridge".

"Fluid medium", as used herein, refers to any liquid that is used in connection with the methods and includes the samples containing the cells, typically suspended in a medium or buffer or in form of a biological fluid, such as blood, urine, saliva and the like, liquid solutions of the detection reagents, washing solutions, and the like. The fluid medium may also be a medium designed to support the growth of cells.

In various embodiments, in which the solid support is part of a closed device as described above, the steps of immobilizing the cells, contacting the cells with detection reagents and optional steps such as fixating the cells, permeating the cells, washing the cells, etc. are performed by delivering a fluid medium comprising the required respective active agents via the inlet to the cells and removing it again by means of the outlet. The contacting may occur by a continuous feed of the respective liquid medium through the device via the inlet and outlet openings.

In various embodiments, the steps (ii)-(vii) of the method are automated. "Automated" in this regard means that the recited steps are controlled or operated by using machines, computers, etc., and do not require the actual intervention of laboratory personnel.

In various embodiments, step (iii) is repeated with each detection cycle. This may allow compensating for variations in the cells' auto-fluorescence, for example caused by extended exposure to light or other factors, by correcting each measurements by a reference measurements performed prior to the actual measurement but after a previous detection reagent measurement.

As also described above, in various embodiments, step (iv) comprises contacting the immobilized cells with a plurality of detection reagents, each comprising (a) a moiety that specifically recognizes and binds a target molecule and (b) a fluorescent label, wherein the detection reagents differ with respect to the target-binding moiety and the fluorescent label, under conditions that allow binding of the detection reagents to their target molecules and wherein steps (v) and (vi) are repeated for each detection reagent/target molecule pair. It is understood that in such embodiments the detection reagents or at least the labels contained therein have to differ sufficiently to allow distinction between the different detection reagents, as also described in more detail above.

While living cells can be analyzed in the methods, in various embodiments, the immobilized cells are denatured, such as by treatment with formalin. The term "formalin", as used herein, relates to a solution of formaldehyde in water, typically at a concentration of 2 to 10 wt.-%, such as 4-8 wt.-%, widely used in histology applications to denature and fixate cells and tissues and even whole organs. "Denaturing", as used herein, primarily refers to the fixation of the cells. Fixation terminates any ongoing biochemical reactions, and may also increase the mechanical strength or stability of the treated cells. The denaturing may further include permeabilization of the cells to ensure free access of the detection reagent to its target molecule, if the latter is located within the cell. For permeabilization organic solvents, such as methanol and acetone, and detergents such as saponin, Triton X-100 and Tween-20, can be used.

The immobilized cells are stored under conditions that inhibit any biological and biochemical processes in the cells in a non-limiting embodiment, such as any metabolic reactions and that also prevent, at least to a certain extent, degradation of the cellular material.

In further various embodiments, the step of determining the position of the individual immobilized cells is carried out using a light optical microscope or is combined with the step of determining the auto-fluorescence of the individual immobilized cells.

In various embodiments, the method can be put into practice based on methology of chip cytometry (Henning, C. et al. (2008), Cytometry Part A, Volume 75A, Issue 4). Without further limitation, the method for single cell analysis by determining the presence and/or amount of one or more target molecules may use ZellSafe microfluidic chips (Zellkraftwerk GmbH, Leipzig, Germany) containing cell-adhesive surfaces, for example to immobilize primary human or mouse hematopoietic cells. After adhesion to the chips, cells can be fixed with PBS-buffered paraformaldehyde for long-term storage. The chips can be (re-)analyzed for biomarker expression and cell loss/changes of cell type composition by Chipcytometry.

To detect the fluorescence signals of the investigated cells, commercially available fluorescence microscopes, such as the Axio Observer.Z1 (Carl Zeiss AG, Oberkochen, Germany) may be used. For cell recognition and position recording computers and specific software components may be used, all of which are readily available in the field or could be obtained by those skilled in the art by known means.

EXAMPLES

Figure 1A:
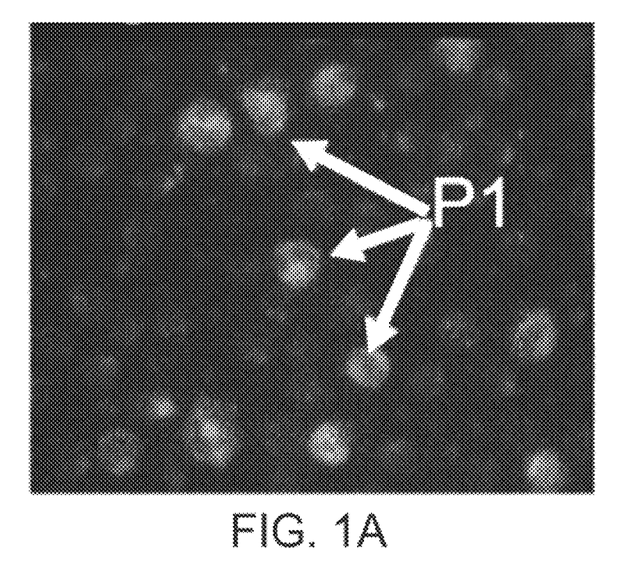
FIG. 1A shows a cutout of an image containing cells prior to treatment with the detection molecule.
Figure 1B:
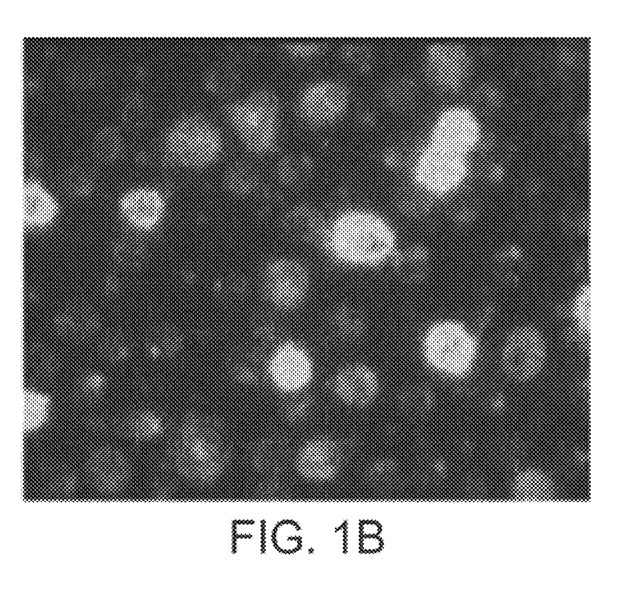
FIG. 1B shows the same cutout as FIG. 1A but after staining with a detection molecule 1.
Figure 1C:
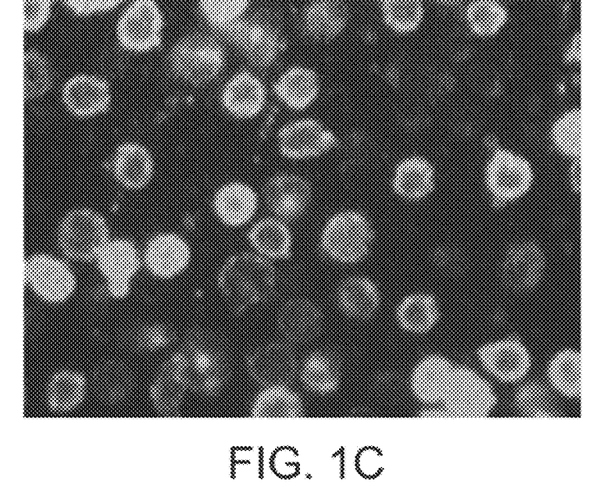
FIG. 1C shows the same cutout as FIG. 1A but after staining with a detection molecule 2.
Figure 2A:
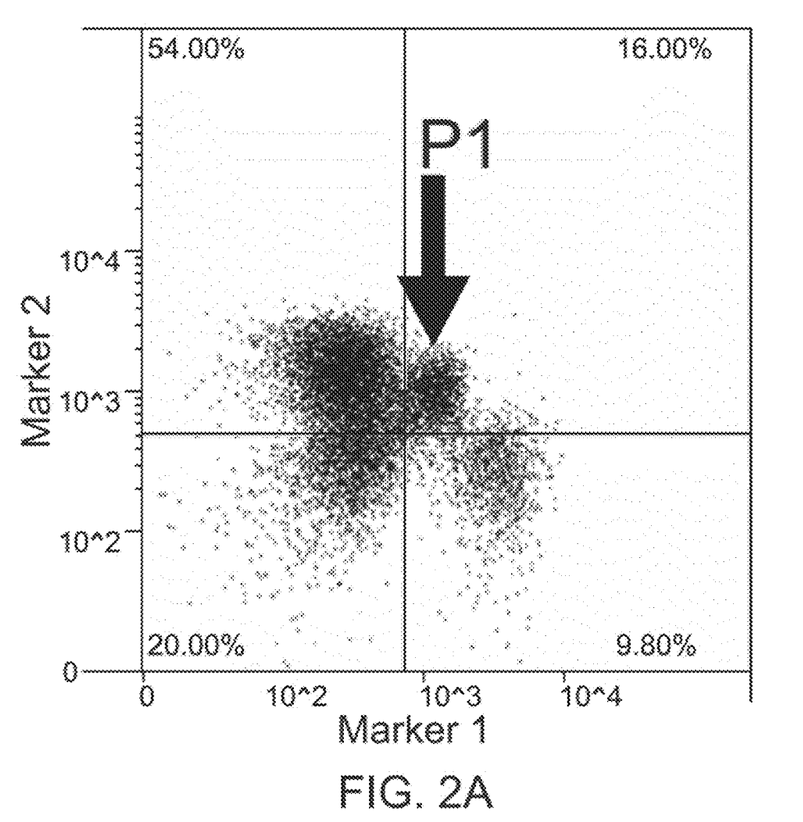
FIG. 2A depicts a cytometry data dot plots from cells without autofluorescence correction.
Figure 2B:
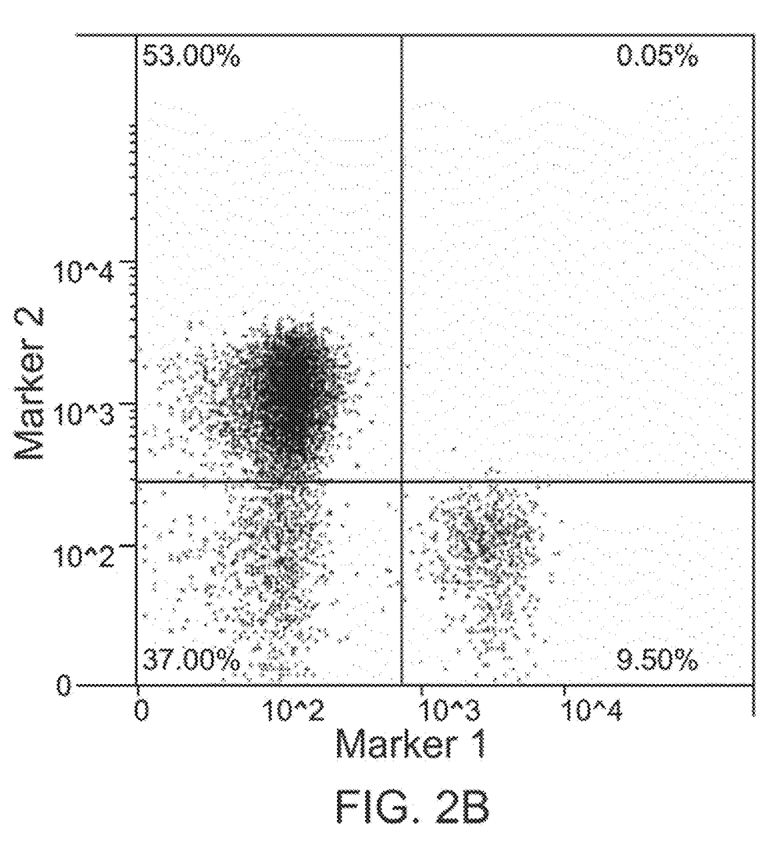
FIG. 2B depicts a method of autofluorescence correction that enhances signal-to-background ration by only measuring a true signal derived from a treatment with a detection molecule.

Example 1: Detection of a Fluorescence Signal of CD 25 with or without Autofluorescence Correction Human peripheral blood mononuclear cells containing highly autofluorescent cells were immobilized on ZellSafe microfluidic chips (Zellkraftwerk GmbH, Leipzig, Germany) and treated as described by Hennig et al. (Hennig, C. et al. (2008), Cytometry Part A, Volume 75A, Issue 4). Fluorescence signals were recorded with the ZellScanner ONE (Zellkraftwerk GmbH, Leipzig, Germany). The fluorescence of cells was measured before each treatment with the detection molecule to determine the autofluorescence background signal of each cell. After treatment with the detection molecules (CD19 and CD3, respectively) the chip was measured again. FIG. 1a shows a cutout of an image containing cells prior to treatment with the detection molecule (thus all signals visible are from autofluorescence) FIGS. 1b and 1c show the same cutout after staining with detection molecule 1 (CD19) and detection molecule 2 (CD3), respectively. Generation of cytometry data dot plots from these cells WITHOUT autofluorescence correction (FIG. 1d) would generate a population of false-positive cells (P1) that very much reduces the signal-to-background ratio for marker 1 (CD19) and 2 (CD3). FIG. 1e shows that the application of the here described method of autofluorescence correction significantly enhances signal-to-background ratio by only measuring the true signal evolving from the treatment with the detection molecule.

The invention has been described broadly and generically herein. Each of the narrower species and subgeneric groupings falling within the generic disclosure also form part of the invention. This includes the generic description of the invention with a proviso or negative limitation removing any subject-matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of non-limiting embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Thus, for example, the terms "comprising", "including," containing", etc. shall be read expansively and without limitation. The word "comprise" or variations such as "comprises" or "comprising" will accordingly be understood to imply the inclusion of a stated integer or groups of integers but not the exclusion of any other integer or group of integers. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

The invention claimed is:

1. A method for single cell analysis by determining the presence and/or amount of one or more target molecules in a plurality of cells, comprising:
   (i) immobilizing the plurality of cells on a solid substrate, wherein the plurality of cells are immobilized in a monolayer form, wherein each individual immobilized cell is sufficiently spaced apart so as to allow the position and focal plane of each individual cell to be determined;
   (ii) determining a position of each immobilized cell of the plurality of cells on the solid substrate;
   (iii) determining an auto-fluorescence background signal of each immobilized cell of the plurality of cells on the solid substrate;

(iv) contacting each immobilized cell immobilized on the solid substrate with at least a first detection reagent comprising:
   (a) a moiety that specifically recognizes and hinds a first target molecule; and
   (b) a fluorescent label;
   wherein the contacting occurs under conditions that allow binding of the at least a first detection reagent to the first target molecule;
(v) measuring a fluorescence of the fluorescent label of each of the at least a first detection reagent bound to the first target molecule of each immobilized cell of the plurality of calls; and
(vi) determining the presence and/or amount of the first target molecule of each individual the immobilized cell of the plurality of cells by comparing the auto-fluorescence background signal of each individual the immobilized cell on the solid substrate with the fluorescence of the fluorescent label of the at least a first detection reagent on a cell-by-cell basis.

2. The method of claim 1, further comprising one or more of:
   photobleaching the at least a first detection reagent,
   quenching the signal of the at least a first detection reagent,
   or combinations thereof.

3. The method of claim 1, further comprising bleaching the immobilized cells prior to steps (iii)-(vi) to decrease auto-fluorescence of the immobilized cells.

4. The method of claim 1, wherein the plurality of cells are eukaryotic cells.

5. The method of claim 4, wherein the eukaryotic cells are hematopoetic cells.

6. The method of claim 1, wherein the one or more target molecules are polypeptide molecules.

7. The method of claim 1, wherein the at least a first detection reagent is an antibody conjugate.

8. The method of claim 1, wherein steps (iv) to (vi) are repeated 1-50 times.

9. The method of claim 1, wherein the plurality of cells immobilized on the solid substrate are non-specifically immobilized on the solid substrate.

10. The method of claim 9, wherein the non-specifically immobilized cells on the solid substrate occur by functionalizing the solid substrate surface with an anionic biomolecule or polymer, and wherein the plurality of cells are contacted with at least a surface of the functionalized solid substrate.

11. The method of claim 1, wherein a surface of the solid substrate surface is functionalized with DNA molecules.

12. The method of claim 1, wherein the solid substrate is configured as part of a device that is at least partially optically transmissive to allow fluorescence detection; wherein the device has an inlet and outlet to allow passage of a fluid medium therethrough.

13. The method of claim 1, wherein the at least a first detection reagent comprises a plurality of different detection reagents, wherein each detection reagent of the plurality of detection reagents comprises:
   (a) a moiety that specifically recognizes and binds a target molecule; and
   (b) a fluorescent label specific to the moiety;
   wherein each detection reagent of the plurality of different detection reagents specifically recognizes and binds a different target molecule, wherein the contacting occurs under conditions that allow binding of the plurality of different detection reagents to each respective target molecule; and
   wherein steps (v) and (vi) are repeated for each detection reagent/target molecule pair of the plurality of different detection reagents.

14. The method of claim 1, wherein the immobilized cells are cells denatured with formalin.

15. The method of claim 1, wherein the determining the position of each of the individual immobilized cells occurs by using a light optical microscope.

16. The method of claim 15, wherein the determining the position of each of the individual immobilized cells further comprises:
   determining the focal plane of each of the individual immobilized cells; and
   recording at least two images of each cell;
   wherein at least one image is taken out-of-focus from the focal plane.

17. The method of claim 1, wherein the determining the position of the individual immobilized cells occurs at substantially the same time as determining the auto-fluorescence background signal of each cell of the individual immobilized cells.

18. The method of claim 1, wherein steps (iv) to (vi) are repeated with a second or further detection reagent comprising:
   (a) a second moiety that specifically recognizes and binds a second or further target molecule that is different from the first target molecule; and
   (b) a fluorescent label specific to the second moiety.

19. The method of claim 1, further comprising removing the at least a first detection reagent after determining the presence and/or amount of the first target molecule of the individual immobilized cells.

* * * * *

UNITED STATES PATENT AND TRADEMARK OFFICE
CERTIFICATE OF CORRECTION

| | |
|---|---|
| PATENT NO. | : 10,955,418 B2 |
| APPLICATION NO. | : 15/708221 |
| DATED | : March 23, 2021 |
| INVENTOR(S) | : Christian Hennig |

It is certified that error appears in the above-identified patent and that said Letters Patent is hereby corrected as shown below:

In the Claims

Column 17, Claim 1, Line 4: "hinds" should read -- binds --.

Column 17, Claim 1, Line 15: should read -- target molecule of each individual immobilized cell --.

Column 17, Claim 1, Lines 17-18: should read -- background signal of each individual immobilized --.

Signed and Sealed this
Nineteenth Day of March, 2024

*Katherine Kelly Vidal*
Katherine Kelly Vidal
*Director of the United States Patent and Trademark Office*